US009050394B2

(12) United States Patent
Carpenter et al.

(10) Patent No.: US 9,050,394 B2
(45) Date of Patent: Jun. 9, 2015

(54) METHOD FOR MAKING TOPOGRAPHICAL FEATURES ON A SURFACE OF A MEDICAL DEVICE

(71) Applicant: Palmaz Scientific, Inc., Dallas, TX (US)

(72) Inventors: Scott P. Carpenter, Fremont, CA (US); Armando Garza, San Jose, CA (US); Julio C. Palmaz, Napa, CA (US)

(73) Assignee: Palmaz Scientific, Inc., Dallas, TX (US)

( * ) Notice: Subject to any disclaimer, the term of this patent is extended or adjusted under 35 U.S.C. 154(b) by 0 days.

(21) Appl. No.: 13/654,923

(22) Filed: Oct. 18, 2012

(65) Prior Publication Data
US 2014/0109383 A1    Apr. 24, 2014

(51) Int. Cl.
| | |
|---|---|
| *A61L 31/00* | (2006.01) |
| *A61L 31/02* | (2006.01) |
| *A61L 31/14* | (2006.01) |
| *A61F 2/00* | (2006.01) |
| *A61F 2/30* | (2006.01) |
| *A61F 2/24* | (2006.01) |
| *A61F 2/915* | (2013.01) |
| *A61F 2/36* | (2006.01) |

(52) U.S. Cl.
CPC .......... *A61L 31/022* (2013.01); *Y10T 29/49982* (2015.01); *A61L 31/14* (2013.01); *A61L 2400/18* (2013.01); *A61F 2/0077* (2013.01); *A61F 2/2418* (2013.01); *A61F 2/915* (2013.01); *A61F 2002/0081* (2013.01); *A61F 2/30771* (2013.01); *A61F 2/36* (2013.01); *A61F 2002/30029* (2013.01); *A61F 2002/3083* (2013.01); *A61F 2002/30838* (2013.01); *A61F 2002/30925* (2013.01)

(58) Field of Classification Search
CPC ..... A61F 2/0077; Y10S 623/901; C23F 1/02; B23C 3/56; C23C 4/185
USPC ........................ 29/527.2; 623/1.15, 1.16, 901
See application file for complete search history.

(56) References Cited

U.S. PATENT DOCUMENTS

| | | | | |
|---|---|---|---|---|
| 3,945,826 | A * | 3/1976 | Friedman et al. | 430/323 |
| 4,549,939 | A * | 10/1985 | Kenworthy et al. | 205/67 |
| 4,733,665 | A | 3/1988 | Palmaz | 128/343 |
| 5,102,417 | A | 4/1992 | Palmaz | 606/195 |
| 5,195,984 | A | 3/1993 | Schatz | 606/195 |
| 5,855,802 | A * | 1/1999 | Acciai et al. | 216/8 |

(Continued)

FOREIGN PATENT DOCUMENTS

| | | | | |
|---|---|---|---|---|
| WO | WO 2012/058491 | | 3/2012 | A61F 2/01 |

OTHER PUBLICATIONS

Hehrlein, et. al., "Influence of surface texture and charge on the biocompatibility of endovascular stents" *Coronary Artery Disease* 6: 581-586 (1995).

(Continued)

*Primary Examiner* — David Bryant
*Assistant Examiner* — Lee A Holly
(74) *Attorney, Agent, or Firm* — David G. Rosenbaum; J. Peter Paredes; Rosenbaum IP, P.C.

(57) ABSTRACT

The invention relates to methods and apparatus for manufacturing medical devices wherein the medical device has a surface treated to promote the migration of cells onto the surface of the medical device. In particular, the surface of the medical device has at least one topographical feature formed therein.

17 Claims, 14 Drawing Sheets

(56) References Cited

U.S. PATENT DOCUMENTS

| | | | | |
|---|---|---|---|---|
| 6,019,784 A | * | 2/2000 | Hines | 128/898 |
| 6,027,863 A | | 2/2000 | Donadio, III | 430/320 |
| 6,146,814 A | | 11/2000 | Millet | 430/320 |
| 6,190,404 B1 | | 2/2001 | Palmaz et al. | 623/1.15 |
| 6,379,383 B1 | | 4/2002 | Palmaz et al. | 623/1.49 |
| 6,797,311 B2 | * | 9/2004 | Loomis et al. | 427/2.24 |
| 6,820,676 B2 | | 11/2004 | Palmaz et al. | 164/46 |
| 6,939,811 B2 | * | 9/2005 | Kamp et al. | 438/734 |
| 7,468,071 B2 | * | 12/2008 | Edwin et al. | 623/1.13 |
| 8,329,021 B2 | | 12/2012 | Garza | 205/666 |
| 2003/0216803 A1 | | 11/2003 | Ledergerber | 623/1.13 |
| 2004/0236398 A1 | | 11/2004 | Burgmeier et al. | 623/1.11 |
| 2007/0003653 A1 | * | 1/2007 | Ahle et al. | 425/174.4 |
| 2008/0055581 A1 | * | 3/2008 | Rogers et al. | 355/95 |
| 2008/0183276 A1 | | 7/2008 | Melder | 623/1.15 |
| 2008/0299337 A1 | | 12/2008 | Glocker et al. | 428/34.1 |
| 2009/0035859 A1 | | 2/2009 | Johnson | 435/402 |
| 2009/0093879 A1 | | 4/2009 | Wawro et al. | 623/11.11 |
| 2009/0304772 A1 | | 12/2009 | Choubey et al. | 424/423 |
| 2011/0276125 A1 | | 11/2011 | Walker et al. | 623/1.15 |
| 2012/0109285 A1 | | 5/2012 | Garza | 623/1.46 |
| 2012/0132612 A1 | | 5/2012 | Banas et al. | 216/8 |
| 2012/0290074 A1 | | 11/2012 | Palmaz | 623/1.36 |

OTHER PUBLICATIONS

Palmaz, J., "The impact of material science and nanotechnology on device innovation in cardiovascular medicine" *TCT* (2010).

Sprague, E., "Impact of stent surface texture and strut thickness: Experimental and clinical evidence" *TCT* (2010).

PCT International Search Report for PCT/US2013/065324, filed Oct. 16, 2013, and published on Apr. 24, 2014 as WO 2014-062854, 5 pages.

International Search Report issued in a corresponding foreign application, pp: 1-3 (Jun. 9, 2014).

* cited by examiner

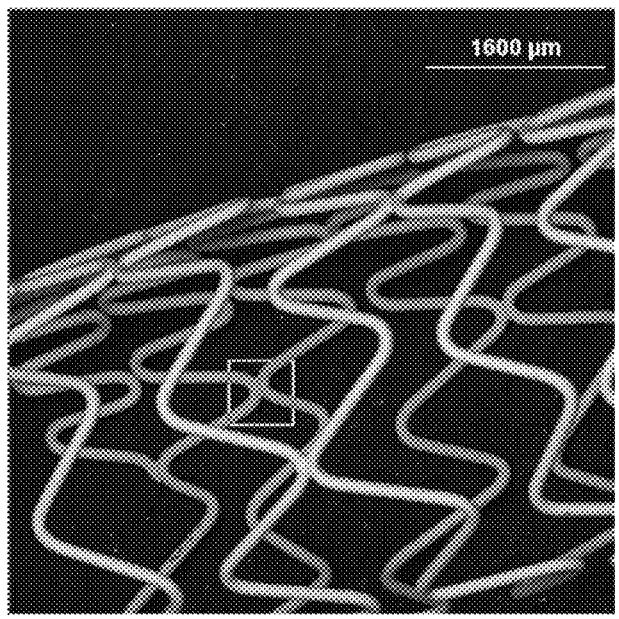
FIGURE 7
FIGURE 8
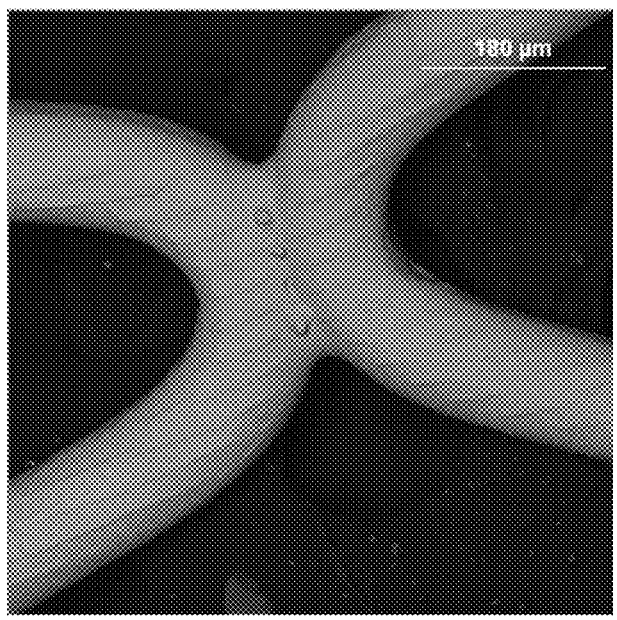

FIGURE 10
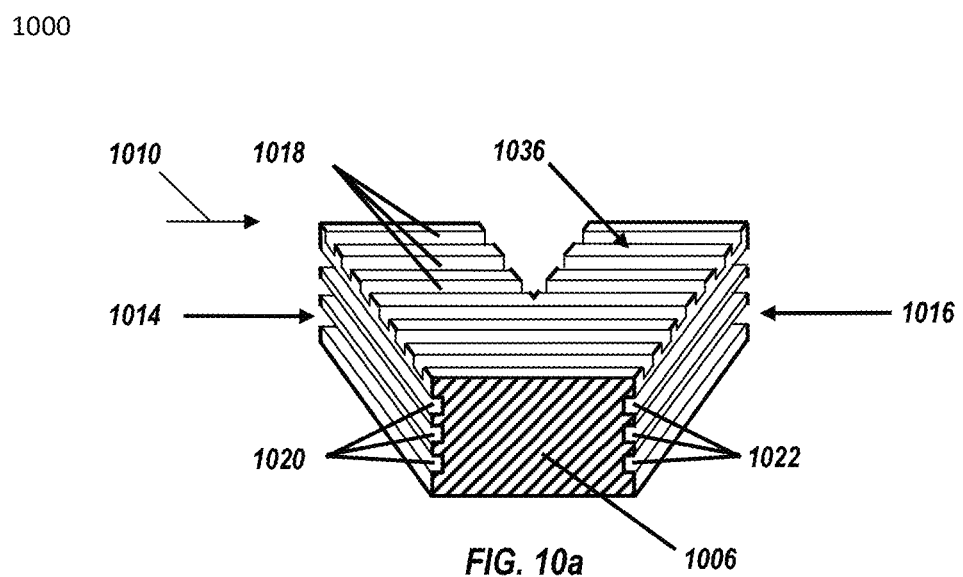
FIG. 10a
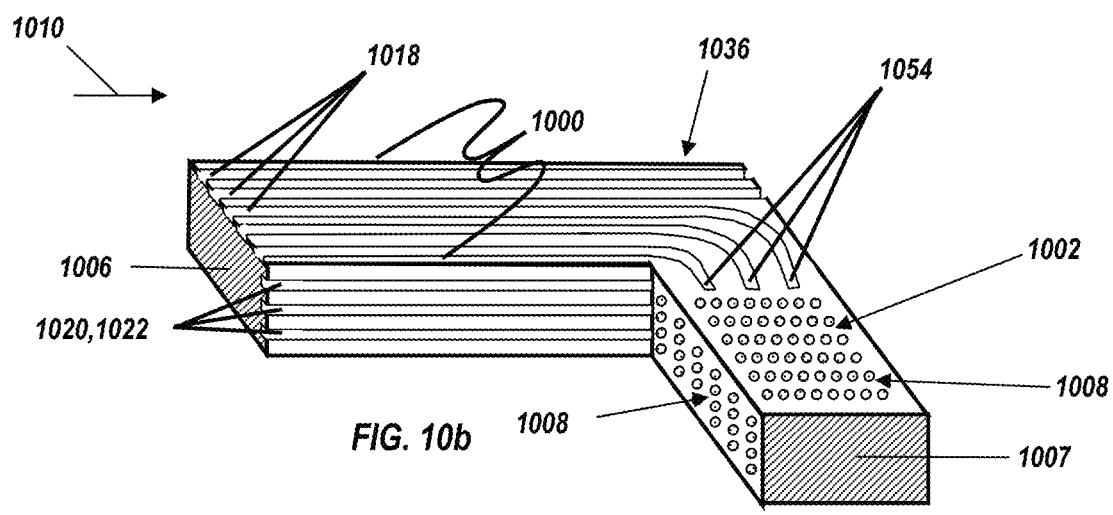
FIG. 10b

METHOD FOR MAKING TOPOGRAPHICAL FEATURES ON A SURFACE OF A MEDICAL DEVICE

CROSS REFERENCE TO RELATED APPLICATIONS

The present application is related to co-pending and commonly owned U.S. patent application Ser. No. 13/103,576, filed May 9, 2011, which is hereby incorporated by reference in its entirety.

BACKGROUND OF THE INVENTION

1. Field of the Invention

The invention relates to methods and apparatus for manufacturing medical devices, wherein the medical device has a surface treated to promote the migration of cells onto the surface of the medical device.

2. Description of Related Art

Various types of intravascular stents have been used in recent years. An intravascular stent generally refers to a device used for the support of living tissue during the healing phase, including the support of internal structures. Intravascular stents, or stents, placed intraluminally, as by use of a catheter device, have been demonstrated to be highly efficacious in initially restoring patency to sites of vascular occlusion. Intravascular stents, or stents, may be of the balloon-expandable type, such as those of U.S. Pat. Nos. 4,733,665; 5,102,417; or 5,195,984, which are distributed by Johnson & Johnson Interventional Systems, of Warren, N.J., as the Palmaz™ and the Palmaz-Schatz™ balloon-expandable stents or balloon expandable stents of other manufacturers, as are known in the art. Other types of intravascular stents are known as self-expanding stents, such as Nitinol coil stents or self-expanding stents made of stainless steel wire formed into a zigzag tubular configuration.

Intravascular stents are used, in general, as a mechanical means to solve the most common problems of percutaneous balloon angioplasty, such as elastic recoil and intimal dissection. One problem intraluminal stent placement shares with other revascularization procedures, including bypass surgery and balloon angioplasty, is restenosis of the artery. An important factor contributing to this possible reocclusion at the site of stent placement is injury to, and loss of, the natural non-thrombogenic lining of the arterial lumen, the endothelium. Loss of the endothelium, exposing the thrombogenic arterial wall matrix proteins, along with the generally thrombogenic nature of prosthetic materials, initiates platelet deposition and activation of the coagulation cascade. Depending on a multitude of factors, such as activity of the fibrinolytic system, the use of anticoagulants, and the nature of the lesion substrate, the result of this process may range from a small mural to an occlusive thrombus. Secondly, loss of the endothelium at the interventional site may be critical to the development and extent of eventual intimal hyperplasia at the site. Previous studies have demonstrated that the presence of an intact endothelial layer at an injured arterial site can significantly inhibit the extent of smooth muscle cell-related intimal hyperplasia. Rapid re-endothelialization of the arterial wall, as well as endothelialization of the prosthetic surface, or inner surface of the stent, are therefore critical for the prevention of low-flow thrombosis and for continued patency. Unless endothelial cells from another source are somehow introduced and seeded at the site, coverage of an injured area of endothelium is achieved primarily, at least initially, by migration of endothelial cells from adjacent arterial areas of intact endothelium.

Although an in vitro biological coating to a stent in the form of seeded endothelial cells on metal stents has been previously proposed, there are believed to be serious logistic problems related to live-cell seeding, which may prove to be insurmountable. Thus, it would be advantageous to increase the rate at which endothelial cells from adjacent arterial areas of intact endothelium migrate upon the inner surface of the stent exposed to the flow of blood through the artery. At present, most intravascular stents are manufactured of stainless steel and such stents become embedded in the arterial wall by tissue growth weeks to months after placement. This favorable outcome occurs consistently with any stent design, provided it has a reasonably low metal surface and does not obstruct the fluid, or blood, flow through the artery. Furthermore, because of the fluid dynamics along the inner arterial walls caused by blood pumping through the arteries, along with the blood/endothelium interface itself, it has been desired that the stents have a very smooth surface to facilitate migration of endothelial cells onto the surface of the stent. In fact, it has been reported that smoothness of the stent surface after expansion is crucial to the biocompatibility of a stent, and thus, any surface topography other than smooth is not desired. Christoph Hehriein, et. al., Influence of Surface Texture and Charge On the Biocompatibility of Endovascular Stents, Coronary Artery Disease, Vol. 6, pages 581-586 (1995). After the stent has been coated with serum proteins, the endothelium grows over the fibrin-coated metal surface on the inner surface of the stent until a continuous endothelial layer covers the stent surface, in days to weeks. Endothelium renders the thrombogenic metal surface protected from thrombus deposition, which is likely to form with slow or turbulent flow. At present, all intravascular stents made of stainless steel, or other alloys or metals, are provided with an extremely smooth surface finish, such as is usually obtained by electropolishing the metallic stent surfaces. Although presently known intravascular stents, specific including the Palmaz™ and Palmaz-Schatz™ balloon-expandable stents have been demonstrated to be successful in the treatment of coronary disease, as an adjunct to balloon angioplasty, intravascular stents could be even more successful and efficacious, if the rate and/or speed of endothelial cell migration onto the inner surface of the stent could be increased. It is believed that providing topographical features disposed on a surface of a medical device increases the rate of migration of cells upon the surface of the medical device after it has been implanted. Accordingly, the art has sought methods and apparatus for manufacturing at least one groove disposed on the surface of the medical device.

SUMMARY OF THE INVENTION

In accordance with the invention, the foregoing advantage has been achieved through the present methods and apparatus for manufacturing a medical device with at least one topographical feature disposed in a surface of the device.

In one embodiment of the present invention, there is provided a method of manufacturing a medical device by first forming a device having at least one surface; and then forming at least one topographical feature on the surface of the device by etching the surface with a chemical process. Preferably, the chemical process may comprise the steps of coating the surface of the device with a photosensitive material; mounting the device on a mask; irradiating the surface of the device by a source of exposing radiation; removing the device from the mask; and etching light exposed areas to produce at least one topographical feature in the surface of the device. The mask may be disposed upon a surface of a transparent apparatus adapted to have the device mounted thereupon, and the device is mounted on the transparent apparatus. The source of exposing radiation may be an ultraviolet light source, but could be a light source with any wavelength compatible with the photosensitive material. Alternatively, the exposing radiation may be atomic in nature. The exposing radiation may be transmitted through one edge of the apparatus, or transmitted by means of a fiber optic cable inserted within the apparatus below the mask. If a fiber optic cable is used, either an end transmitting fiber optic cable may be translated within the apparatus to gain even exposures, or a bare (preferably frosted) fiber may be used to broadcast the exposing radiation from within the apparatus. After exposure, the device is removed from the apparatus. The photosensitive material is developed to reveal the pattern imparted by the mask by exposing the base material of the device through the use of appropriate chemicals. The exposed base material of the device may then be chemically machined to a desired depth. The machining may be accomplished by wet or dry chemical etching or polishing, or by electrochemical machining.

In another embodiment of the present invention, after machining, the patterning and machining process can be repeated with additional masks to achieve multi-depth topographical features on the device.

In another embodiment of the present invention, after machining, the remaining photosensitive material may be chemically or mechanically removed from the device.

In another embodiment of the present invention, the machined pattern may be used to enhance bone formation by enhancing osteoblast production, such as for orthopedic or dental devices.

In another embodiment of the present invention, the machined pattern may include features which pin or demote cell proliferation. These patterns may be used to steer cells to control a directionality of healing response. Any type of cell is encompassed by the present invention, which have a cellular membrane. Most distinct cell types arise from a single totipotent cell that differentiates into hundreds of different cell types during the course of development. Multicellular organisms are composed of cells that fall into two fundamental types: germ cells and somatic cells. During development, somatic cells will become more specialized and form the three primary germ layers: ectoderm, mesoderm, and endoderm. After formation of the three germ layers, cells will continue to specialize until they reach a terminally differentiated state that is much more resistant to changes in cell type than its progenitors. The ectoderm differentiates to form the nervous system (spine, peripheral nerves and brain), tooth enamel and the epidermis (the outer part of integument). It also forms the lining of mouth, anus, nostrils, sweat glands, hair and nails. The endoderm forms the gastrointestinal tract cells, the respiratory tract cells, the endocrine glands and organ cells, the auditory system cells, and the urinary system cells. The mesoderm forms mesenchyme (connective tissue), mesothelium, non-epithelial blood cells and coelomocytes. Mesothelium lines coeloms; forms the muscles, septa (crosswise partitions) and mesenteries (length-wise partitions); and forms part of the gonads (the rest being the gametes).

In one embodiment, a first pattern may be applied to a first surface of a dental implant, and a second pattern may be applied to a second surface of the dental implant. The first surface may serve to promote adhesion and healing of the implant in the bony part of the jaw, while the second surface may serve to stop proliferation of bone into the gum line.

Additional applications where it may be advantageous to demote healing include, without limitation, temporary implants such as a vena cava filter or an insulin pump needle.

In one embodiment of the present invention, there is provided a method of manufacturing a photomask transparent apparatus by first providing a transparent apparatus; then coating the transparent apparatus with an opaque layer; and then removing portions of the opaque layer such that exposing radiation may be transmitted through the transparent apparatus in the regions where the opaque layer has been removed. The transparent apparatus has at least one surface adapted to have medical device mounted thereupon. The transparent apparatus may comprise quartz, glass, or any other material capable of transmitting the exposing radiation. In one embodiment, the opaque layer is a thin wall disposed against the surface of the transparent apparatus. In another embodiment, the opaque layer may be a metal, a polymer, a composite, a ceramic, or any other material that sufficiently blocks the transmission of the exposing radiation. The opaque layer may be deposited by several methods, including: dipping, spraying, vapor deposition, plating, or painting. The opaque layer may be selectively removed from the transparent apparatus by appropriate means, including laser ablation, mechanical means, photolithography, etching, or engraving, and/or the like. The selective removal of the opaque layer results in a photomask pattern on the surface of the transparent apparatus, such pattern capable of being imparted to a photoresist coated medical device through a photolithography process.

In one embodiment of the present invention, there is provided a method of manufacturing a metallic intravascular stent by first forming a stent having an inner surface and an outer surface; and then forming at least one topographical feature on the inner surface of the stent by etching the inner surface with a chemical process. Preferably, the chemical process may comprise the steps of coating the inner surface of the stent with a photosensitive material; providing a mandrel having a photomask disposed thereon; mounting the stent on the mandrel; irradiating the inner surface of the stent by a source of exposing radiation; removing the sten from the mandrel; and etching exposed areas to produce at least one topographical feature in the inner surface of the stent. The photomask may be an opaque layer disposed upon a surface of a transparent mandrel adapted to have the stent mounted thereupon, and the stent is mounted on the transparent mandrel. The source of exposing radiation may be an ultraviolet light source, but could be a light source with any wavelength compatible with the photosensitive material. Alternatively, the exposing radiation may be atomic in nature. The exposing radiation may be transmitted through the end of the mandrel, or transmitted by means of a fiber optic cable inserted into the interior of the mandrel. If a fiber optic cable is used, either an end transmitting fiber optic cable may be translated through the mandrel to gain even exposures, or a bare (preferably frosted) fiber may be used to broadcast the exposing radiation from within the mandrel. After exposure, the stent is removed from the mandrel. The photosensitive material is developed to reveal the pattern imparted by the photomask by exposing the base material of the stent through the use of appropriate chemicals. The exposed base material of the stent may then be chemically machined to a desired depth. The machining may be accomplished by wet or dry chemical etching or polishing, or by electrochemical machining.

In one embodiment of the present invention, the photosensitive material is either a positive or negative photoresist, such as InterVia™ 3D-P Photoresist (PEPR-2400), manufactured by MicroChem.

In another embodiment of the present invention, after machining, the patterning and machining process can be repeated with additional masks to achieve multi-depth topographical features on the stent.

In another embodiment of the present invention, after machining, the remaining photosensitive material may be chemically or mechanically removed from the stent.

In one embodiment of the present invention, there is provided a method of manufacturing a photomask mandrel by first providing a transparent mandrel; then coating the transparent mandrel with an opaque layer; and then removing portions of the opaque layer such that exposing radiation may be transmitted through the transparent mandrel in the regions where the opaque layer has been removed. The transparent mandrel is preferably cylindrical in shape, but may be tapered and/or have a polygonal cross section. The transparent mandrel may comprise quartz, glass, or any other material capable of transmitting the exposing radiation. In one embodiment, the opaque layer is a thin wall tube within or without the transparent mandrel. In another embodiment, the opaque layer may be a metal, a polymer, a composite, a ceramic, or any other material that sufficiently blocks the transmission of the exposing radiation. The opaque layer may be deposited by several methods, including: dipping, spraying, vapor deposition, plating, or painting. The opaque layer may be selectively removed from the transparent mandrel by appropriate means, including laser ablation, mechanical means, photolithography, etching, or engraving, and/or the like. The selective removal of the opaque layer results in a photomask pattern on the surface of the transparent mandrel, such pattern capable of being imparted to a photoresist coated intravascular stent through a photolithography process.

In any embodiment of the present invention, an existing medical device, stent, or other article may be utilized. Through the use of an existing structure, it is likely that the regulatory path may be minimized. Particular, non-limiting devices include dental implants and hip implants.

It is believed that the improvements in methods and apparatus for manufacturing medical devices of the present invention, when compared with presently known methods for manufacturing such devices, has the advantage of increasing the rate of migration of cells upon the surface of the medical device.

BRIEF DESCRIPTION OF THE DRAWINGS

FIGS. 7 and 8 are scanning electron microscope images of a cobalt chrome alloy wire stent upon which the inventive method has been practiced to create topographical features.

FIG. 10a is an illustration of one embodiment of an implantable medical device having surfaces imparted with topographical features by the inventive method; FIG. 10b is an illustration of one embodiment of an implantable medical device having surfaces imparted with topographical features by the inventive method, wherein the features include directional grooves and dots/pins.

FIG. 11b is an enlarged view of a portion of the dental implant of FIG. 11a.

FIG. 12b is an enlarged view of a portion of the hip implant of FIG. 12a; and FIG. 12c is an enlarged view of a distal portion of the hip implant of FIG. 12a.

FIG. 13b is an enlarged view of a portion of the heart valve of FIG. 13a.

While the invention will be described in connection with the preferred embodiment, it will be understood that it is not intended to limit the invention of that embodiment. On the contrary, it is intended to cover all alternatives, modifications, and equivalents, as may be included within the spirit and scope of the invention as defined by the appended claims.

DETAILED DESCRIPTION OF THE INVENTION

Figure 1:
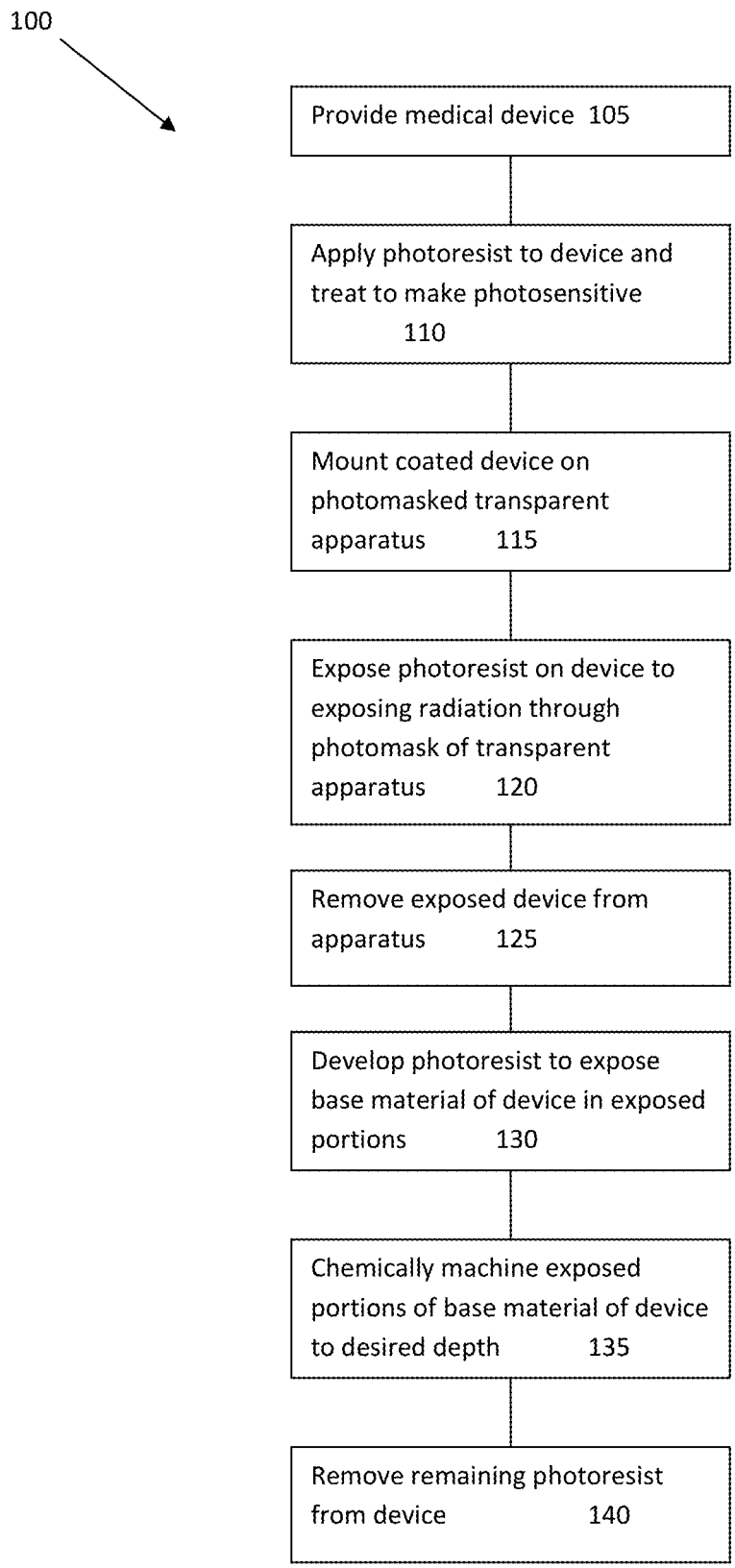
FIG. 1 is a block diagram illustrating a method of manufacturing a medical device having at least one topographical feature created on a surface thereof by the inventive method.

With reference to FIG. 1, the method of creating structural features on a surface of a medical device 100 is illustrated. First, a medical device is provided 105. In a preferred embodiment, the medical device is metallic in nature, but need only be suitable for chemical machining Photoresist is then applied to the device and treated appropriately to make the photoresist photosensitive 110. In a preferred embodiment, the photoresist is an electrodeposited positive photoresist (InterVi™ 3D-P Photoresist PEPR-2400) from Micro-Chem. Alternative photoresists are contemplated by and within the scope of this disclosure, including negative photoresist. By electrodepositing the photoresist, all surfaces of the device are easily coated with a uniform layer of resist, as compared to traditional photoresist application methods. It is important to attain sufficient control over coating thickness on especially the inner diameter of the stent. In alternative embodiments, the device may be coated with photoresist by dipping, spraying, spinning, electrodeposition, or any other typical means of applying photoresist. Once the device is coated, the device is mounted on a photomasked transparent apparatus 115. The method of creating the photomasked transparent apparatus is discussed further below, in relation to FIG. 3. In mounting the device on the photomasked apparatus, it is preferable to maintain intimate contact between the device and apparatus, to aid in pattern transfer. In one embodiment, an external force is applied to the device to obtain this intimate contact. In another embodiment, an interference fit between the apparatus and the device can be used to obtain the intimate contact. In embodiments where the device is nitinol-based, the interference fit may be obtained by shape memory. Once the device is mounted on the apparatus, the photoresist coating on the device is exposed to exposing radiation through the photomasked apparatus 120. In a preferred embodiment, the exposing radiation is an ultraviolet light source, though the light source could have any wavelength that is compatible with the particular photoresist utilized by the inventive method. One such source is a light guide or an internal 0.7 mm fiber with UV radiation provided by a 200W Lesco SuperSpot Max-HP source. In an alternative embodiment, the exposing radiation may be atomic in nature. The exposing radiation may be transmitted through one edge of the apparatus, or transmitted by means of a fiber optic cable inserted within the apparatus below the photomask. If a fiber optic cable is used, either an end transmitting fiber optic cable may be translated within the apparatus to gain even exposures, or a bare (preferably frosted) fiber may be used to broadcast the exposing radiation from within the apparatus. After exposure, the now exposed device is removed from the apparatus 125. The exposed photoresist is then developed to reveal the pattern imparted by the photomask 130. In the preferred embodiment, using a positive photoresist, developing exposes the base material of the device in the exposed portions of the photoresist through the use of appropriate chemicals. In the preferred embodiment, the appropriate chemicals are those recommended by the manufacturer of the photoresist, including InterVia™ 3D-P Developer, InterVia™ 3D-P Remover, InterVia™ 3D-P Solvent, and InterVia™ 3D-P TC. The exposed base material of the device may then be chemically machined to a desired depth 135. The machining may be accomplished by wet or dry chemical etching or polishing, or by electrochemical machining. In one embodiment, the electrochemical methods are carried out in a phosphoric acid bath. Once the machining is complete, the remaining photoresist may be removed from the device 140, by appropriate means. Appropriate means may include chemical or mechanical removal of the remaining photoresist. The result is a medical device having structural features created on at least one surface of the device.

In a further embodiment, after the machining is complete, the patterning and machining process can be repeated using additional transparent apparatuses, having distinct photomask patterns, to achieve multiple-depth structural features on the surface of the device.

Figure 2:
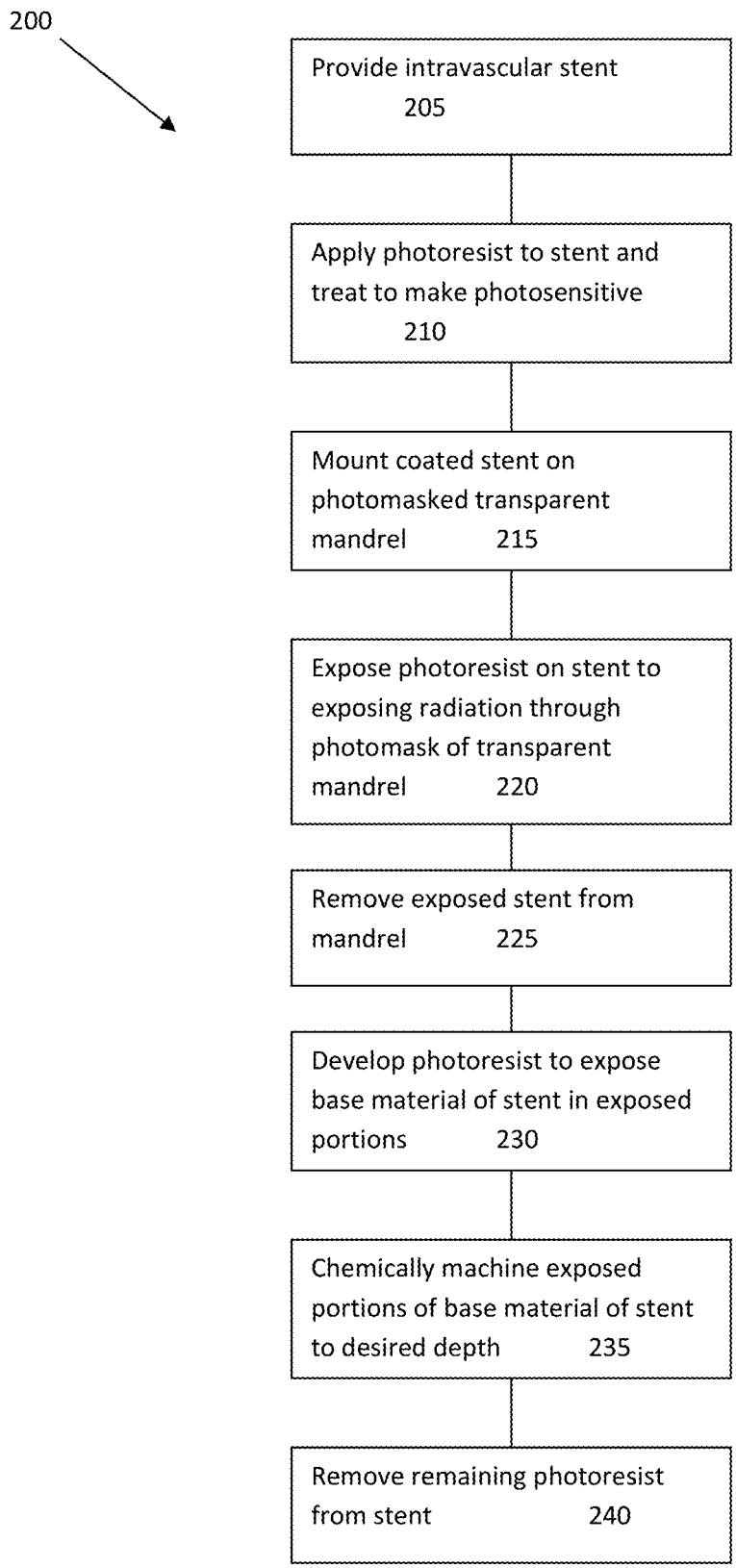
FIG. 2 is a block diagram illustrating a method of manufacturing an intravascular stent having at least one topographical feature created on the inner surface thereof by the inventive method.

With reference to FIG. 2, the method of creating structural features on the inner diameter surface of an intravascular stent 200 is illustrated. First, an intravascular stent is provided 205. In a preferred embodiment, the intravascular stent is metallic in nature, but the material of the intravascular stent need only be suitable for chemical machining. Photoresist is then applied to the stent and treated appropriately to make the photoresist photosensitive 210. In a preferred embodiment, the photoresist is an electrodeposited positive photoresist (InterVia™ 3D-P Photoresist PEPR-2400) from MicroChem. Alternative photoresists are contemplated by and within the scope of this disclosure, including negative photoresist. If a negative photoresist is used, additional steps are required to expose the masked portions of the stent and then expose the remaining surfaces. By electrodepositing the photoresist, all surfaces of the stent are easily coated with a uniform layer of resist, as compared to traditional photoresist application methods. It is important to attain sufficient control over coating thickness on especially the inner diameter of the stent. In alternative embodiments, the stent may be coated with photoresist by dipping, spraying, spinning, electrodeposition, or any other typical means of applying photoresist. Once the stent is coated, the stent is mounted on a photomasked transparent mandrel 215. The method of creating the photomasked transparent mandrel is discussed further below, in relation to FIG. 4. In mounting the stent on the photomasked mandrel, it is preferable to maintain intimate contact between the stent and the mandrel, to aid in pattern transfer. In one embodiment, an external force is applied to the stent to obtain this intimate contact. In another embodiment, an interference fit between the mandrel and the stent can be used to obtain the intimate contact. In embodiments where the stent is nitinol-based, the interference fit may be obtained by shape memory. Once the stent is mounted on the mandrel, the photoresist coating on the stent is exposed to exposing radiation through the photomasked mandrel 220. In a preferred embodiment, the exposing radiation is an ultraviolet light source, though the light source could have any wavelength that is compatible with the particular photoresist utilized by the inventive method. One such source is a light guide or an internal 0.7 mm fiber with UV radiation provided by a 200W Lesco SuperSpot Max-HP source. In an alternative embodiment, the exposing radiation may be atomic in nature. The exposing radiation may be transmitted through one end of the mandrel, or transmitted by means of a fiber optic cable inserted within the mandrel below the photomask. If a fiber optic cable is used, either an end transmitting fiber optic cable may be translated within the mandrel to gain even exposures, or a bare (preferably frosted) fiber may be used to broadcast the exposing radiation from within the mandrel. After exposure, the now exposed stent is removed from the mandrel 225. The exposed photoresist is then developed to reveal the pattern imparted by the photomask 230. In the preferred embodiment, using a positive photoresist, developing exposes the base material of the stent in the exposed portions of the photoresist through the use of appropriate chemicals. In the preferred embodiment, the appropriate chemicals are those recommended by the manufacturer of the photoresist, including InterVia™ 3D-P Developer, InterVia™ 3D-P Remover, InterVia™ 3D-P Solvent, and InterVia™ 3D-P TC. The exposed base material of the stent may then be chemically machined to a desired depth 235. The machining may be accomplished by wet or dry chemical etching or polishing, or by electrochemical machining. In one embodiment, the electrochemical methods are carried out in a phosphoric acid bath. Once the machining is complete, the remaining photoresist may be removed from the stent 240, by appropriate means. Appropriate means may include chemical or mechanical removal of the remaining photoresist. The result is an intravascular stent having structural features created on an inner diameter surface of the stent.

Figure 3:
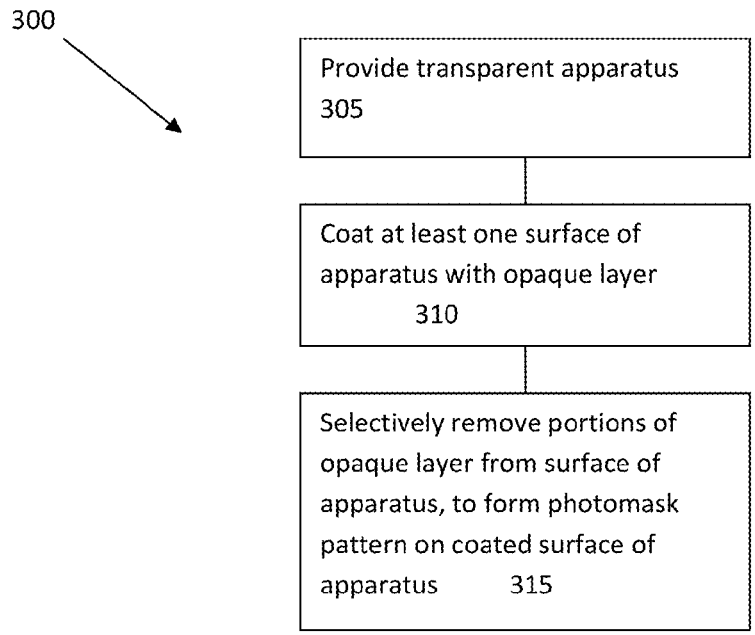
FIG. 3 is a block diagram illustrating a method of manufacturing a transparent apparatus having a surface adapted to mount a medical device thereupon, so as to impart a photomask pattern to a surface of the medical device.

With reference to FIG. 3, the method of manufacturing a photomasked transparent apparatus 300 is illustrated. First, a transparent apparatus is provided 305. In a preferred embodiment, the transparent apparatus is comprised of quartz, glass, or any other material capable of transmitting an exposing radiation through a photomask onto a photoresist coated medical device. The transparent apparatus has at least one surface adapted to mount a medical device thereupon. The at least one surface of the transparent apparatus is then coated with an opaque layer 310. In one embodiment, the opaque layer is a thin wall material on the top or bottom of the at least one surface. In another embodiment, the opaque layer may be a metal, a polymer, a composite, a ceramic, or any other material that sufficiently blocks the transmission of the exposing radiation. The opaque layer may be deposited by several methods, including: dipping, spraying, vapor deposition, plating, or painting. Once coated, portions of the opaque layer may be selectively removed from the transparent apparatus by appropriate means 315, so as to form a photomask pattern on the surface of the apparatus. The appropriate means may include laser ablation, mechanical means, photolithography, etching, or engraving, and/or the like. With portions of the opaque layer removed, an exposing radiation is able to be transmitted through the now photomasked surface of the transparent apparatus.

Figure 4:
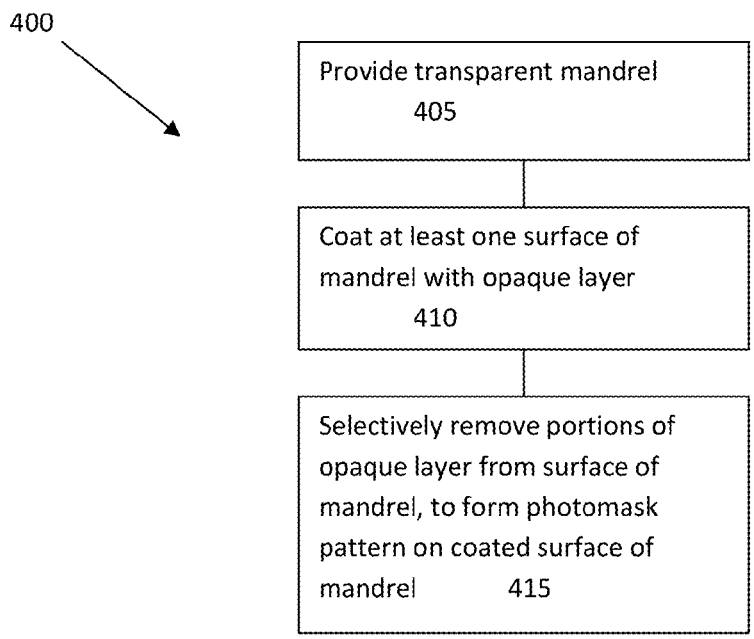
FIG. 4 is a block diagram illustrating a method of manufacturing a transparent mandrel for mounting an intravascular stent thereon, so as to impart a photomask pattern to the inner surface of the stent.

With reference to FIG. 4, the method of manufacturing a photomasked transparent apparatus 400 is illustrated. First, a transparent mandrel is provided 405. In a preferred embodiment, the transparent mandrel is comprised of quartz, glass, or any other material capable of transmitting an exposing radiation through a photomask onto a photoresist coated intravascular stent. In one embodiment, the mandrel is a cylindrical tube or rod. In alternative embodiments, the mandrel may be tapered, have an elliptical cross section, or have a polygonal cross section. The transparent mandrel has at least one surface adapted to mount an intravascular stent thereupon. In one embodiment, the mandrel has at least one open end, within which a fiber optic cable may be inserted for transmittal of the exposing radiation from within the mandrel through a photomask on the exterior of the mandrel. The at least one surface of the transparent mandrel is then coated with an opaque layer 410. In one embodiment, the opaque layer is a thin wall tube disposed against the inner or outer surface of the cylindrical mandrel. In another embodiment, the opaque layer may be a metal, a polymer, a composite, a ceramic, or any other material that sufficiently blocks the transmission of the exposing radiation. The opaque layer may be deposited by several methods, including: dipping, spraying, vapor deposition, plating, or painting. In the preferred embodiment, a metallic coating is deposited by physical vapor deposition on the outer surface of a cylindrical quart tube. Once coated, portions of the opaque layer may be selectively removed from the transparent mandrel by appropriate means 415, so as to form a photomask pattern on the surface of the mandrel. The appropriate means may include laser ablation, mechanical means, photolithography, etching, or engraving, and/or the like. In the preferred embodiment, the opaque layer is removed by laser ablation, utilizing a femtosecond laser cutting system. With portions of the opaque layer removed, an exposing radiation is able to be transmitted through the now photomasked surface of the transparent mandrel.

Figure 9:
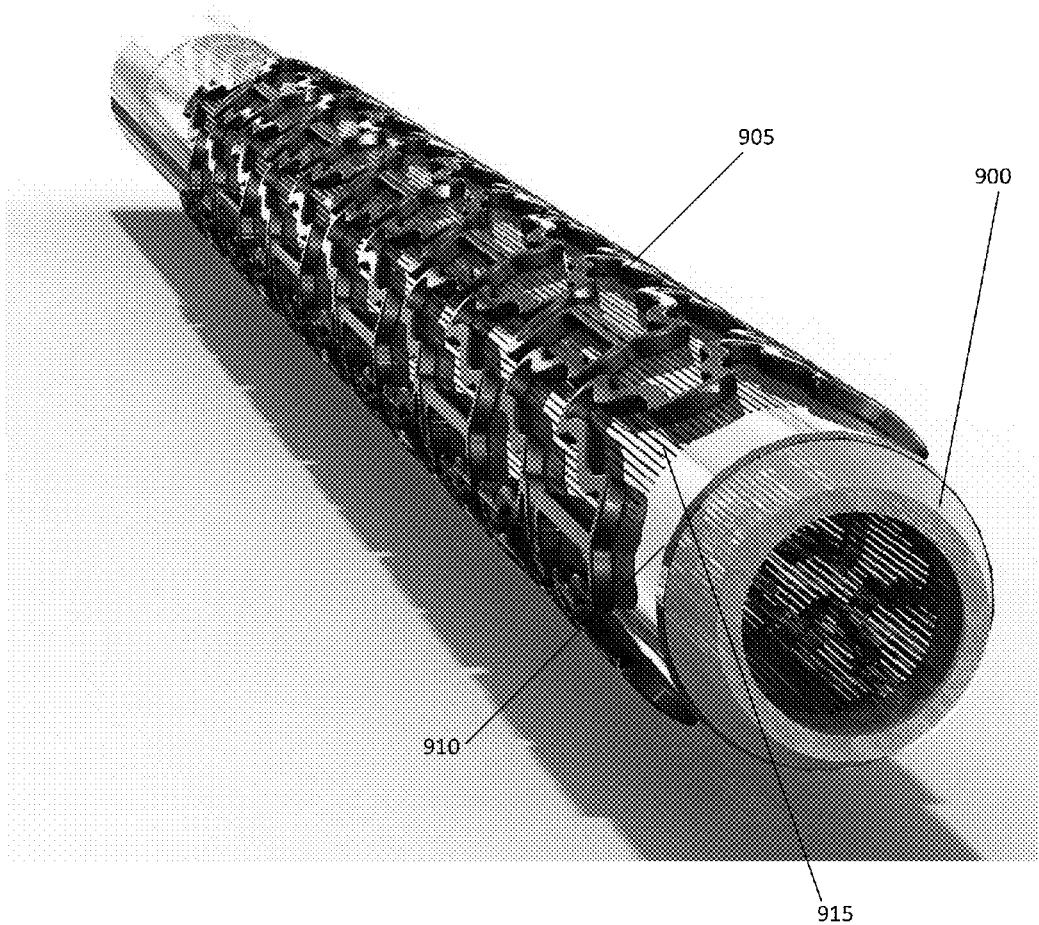
FIG. 9 is an illustration of one embodiment of the transparent mandrel of the present invention, having a photoresist coated stent mounted thereupon.

With reference to FIG. 9, one embodiment of the photomasked transparent mandrel having a photoresist coated stent is depicted. The transparent mandrel 900 is has a photoresist coated intravascular stent 905 mounted on the outer surface of the mandrel. The outer surface of the mandrel is coated with an opaque layer 910. Portions of the opaque layer 910 have been selectively removed to form a mask pattern, the mask pattern comprising openings 915 where the opaque layer has been removed.

In another embodiment of the present invention, the machined pattern may be used to enhance bone formation by enhancing osteoblast production for devices such as, but without limitation to, orthopedic or dental devices.

Referring to FIG. 10A, a structural member 1006 includes a luminal surface 1036 as well as a leading edge 1014 and a trailing edge 1016 relative to the direction 1010 of blood flow. Any or all of the luminal surface 1036, the leading edge 1014, and the trailing edge 1016 may include topographical features disposed therein or thereon. For example, in one embodiment, the topographical features of luminal surface 1036 may be grooves 1018 disposed therein. The grooves 1018 may be oriented in any direction relative to the direction 1010 of blood flow; however, orientation of the grooves 1018 parallel to the direction 1010 of blood flow, as illustrated in FIG. 10A, exposes EC within the grooves 1018 to shear stress caused by the blood flow. As noted hereinabove, such exposure of EC to shear stress increases the rate of migration of the EC.

The leading edge 1014 of the structural member 1006, in one embodiment, may have topographical features such as grooves 1020 disposed therein or thereon. The grooves 1020 may be oriented in any direction relative to the direction 1010 of blood flow. In one embodiment as illustrated in FIG. 10A, the grooves 1020 are oriented such that a component of blood flow along the leading edge 1014 exposes EC within the grooves 1020 to shear stress caused by the blood flow. Similarly, the trailing edge 1016 of the structural member 1006, in one embodiment, may have topographical features such as grooves 1022 disposed therein or thereon. The grooves 1022 may be oriented in any direction relative to the direction 1010 of blood flow. In one embodiment as illustrated in FIG. 10A, the grooves 1022 are oriented such that a component of blood flow along the trailing edge 1016 exposes EC within the grooves 1022 to shear stress caused by the blood flow.

It should be noted that the topographical features on one or more of the surfaces 1036, 1014, 1016, may take any of a variety of forms, and are not limited to the grooves discussed above. For example, any or all of the grooves 1018, 1020, 1022 illustrated in FIG. 10A may alternatively be dots, divots, pores, holes, complex geometries, and/or the like.

Any of the geometrically functional features or recesses may also be included in the trailing edge, leading edge, or surface regions to enhance the endothelial migration and attachment to such surfaces.

An implantable device may include problematic surfaces that may be resistant to endothelialization or may otherwise be relatively slow to endothelialize. The problematic surfaces may be disadvantaged for cell adhesion because of, for example, hemodynamic reasons such as disruption via turbulence or low shear stress (which may occur in thick stents, for example, greater than about 100 μm) or chemical reasons such as anti-mitotic and/or anti-inflammatory drugs. The problematic surfaces could be, for example, stent bridges disposed at various angles against the blood flow.

Referring to FIG. 10b, it is contemplated that a combination of properly oriented grooves may facilitate EC migration to the problematic surfaces and/or promote cell stability thereon. For example, in one embodiment, a main highway 1000 of the grooves 1018 may be disposed in the luminal surface 1036 of the structural member 1006 and oriented generally parallel to the direction 1010 of blood flow, as illustrated in FIG. 10b. The main highway 1000 could provide an abundance of migrating EC, which could be diverted therefrom to a problematic surface, for example, a surface 1002 on a transversely disposed structural member 1007 of the implantable device. For example, the main highway 1000 may be diverted to groove endpoints 1054 on the transversely disposed structural member 1007 of the implantable device.

It is further contemplated that diversion of migrating EC from the main highway 1000 could be applied to surfaces having a specific function, which may or may not otherwise be conducive to EC migration. In some embodiments, the machined pattern may include features which pin or demote cell proliferation, so as to stop cell proliferation in a particular location. These patterns may be used to steer cells to control a directionality of healing response. In some embodiments, and without limitation, these features may be pores, holes, divots, and/or the like. FIG. 10b illustrates one embodiment of a surface with directional and pinning topographical features created thereupon by the inventive method. For example, referring to FIG. 10B, the structural member 1007 may include surfaces including a plurality of pores 1008 as might be found, for example, in a drug eluting stent. The plurality of pores may act to pin cell proliferation in the location of the pores 1008, and demote proliferation beyond the location of pores 1008.

In another embodiment of the present invention, the machined pattern may include features which pin or demote cell proliferation. These patterns may be used to steer cells to control a directionality of healing response. FIG. 10*b* illustrates one embodiment of a surface with directional topographical features created thereupon by the inventive method.

In one embodiment, a first pattern may be applied to a first surface of a dental implant, and a second pattern may be applied to a second surface of the dental implant. The first surface may serve to promote adhesion and healing of the implant in the bony part of the jaw, while the second surface may serve to stop proliferation of bone into the gum line.

Additional applications where it may be advantageous to demote healing include, without limitation, temporary implants such as a vena cava filter or an insulin pump needle.

EXAMPLE 1

Stainless Steel Stent

In one example, the inventive method was applied to a stent made from stainless steel tubing. The material comprising the stent was 316 LVM stainless steel. The stent was coated with electrodeposited (ED) positive photoresist (PEPR-2400) from MicroChem. The coating was treated to make the photoresist photosensitive, and the stent was then mounted on a prepared photomasked transparent mandrel. Exposure was achieved using either a light guide or an internal 0.7 mm fiber with UV radiation provided by a 200W Lesco SuperSpot Max-HP source. Once exposure was complete, the stent was removed from the mandrel and the photoresist was developed using InterVia™ 3D-P Developer. After developing, the exposed portions of the photoresist were machined using electrochemical methods in a phosphoric acid bath. Once machining was complete, the remaining photoresist was removed from the stent using InterVia™ 3D-P ancillary chemicals, recommended by MicroChem.

Figure 5:
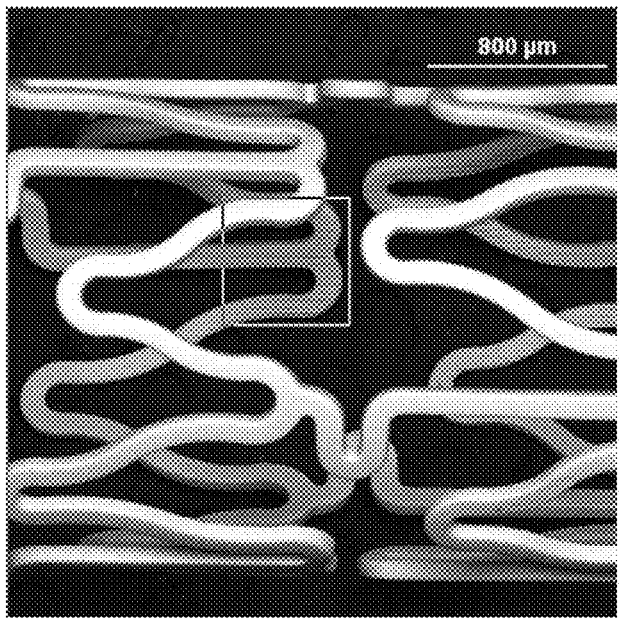
FIGS. 5 and 6 are scanning electron microscope images of a stainless steel stent upon which the inventive method has been practiced to create topographical features.
Figure 6:
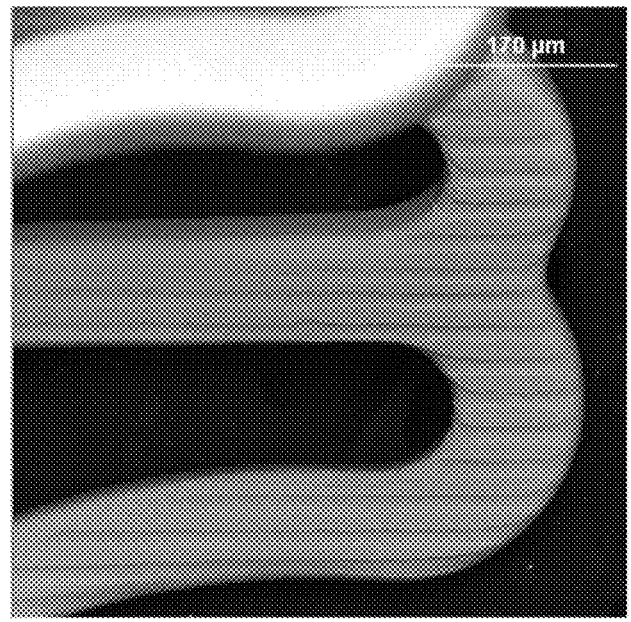

FIGS. 5 and 6 are scanning electron microscope images of the stainless steel stent of Example 1 after the inventive method was applied.

EXAMPLE 2

Cobalt Chrome Alloy Wire Stent

In one example, the inventive method was applied to a stent made from cobalt chrome alloy wire. The stent was an existing Driver® stent provided by Medtronic. The stent was coated with electrodeposited (ED) positive photoresist (PEPR-2400) from MicroChem. The coating was treated to make the photoresist photosensitive, and the stent was then mounted on a prepared photomasked transparent mandrel. Exposure was achieved using either a light guide or an internal 0.7mm fiber with UV radiation provided by a 200W Lesco SuperSpot Max-HP source. Once exposure was complete, the stent was removed from the mandrel and the photoresist was developed using InterVia™ 3D-P Developer. After developing, the exposed portions of the photoresist were machined using electrochemical methods in a phosphoric acid bath. Once machining was complete, the remaining photoresist was removed from the stent using InterVia™ 3D-P ancillary chemicals, recommended by MicroChem.

FIGS. 7 and 8 are scanning electron microscope images of the cobalt chrome alloy wire stent of Example 2 after the inventive method was applied.

In any embodiment of the present invention, an existing medical device, stent, or other article may be utilized. Through the use of an existing structure, it is likely that the regulatory path may be minimized.

Particular, non-limiting examples of medical devices that may be worked upon by the inventive method disclosed herein include dental implants, hip implants, and valves.

Figure 11A:
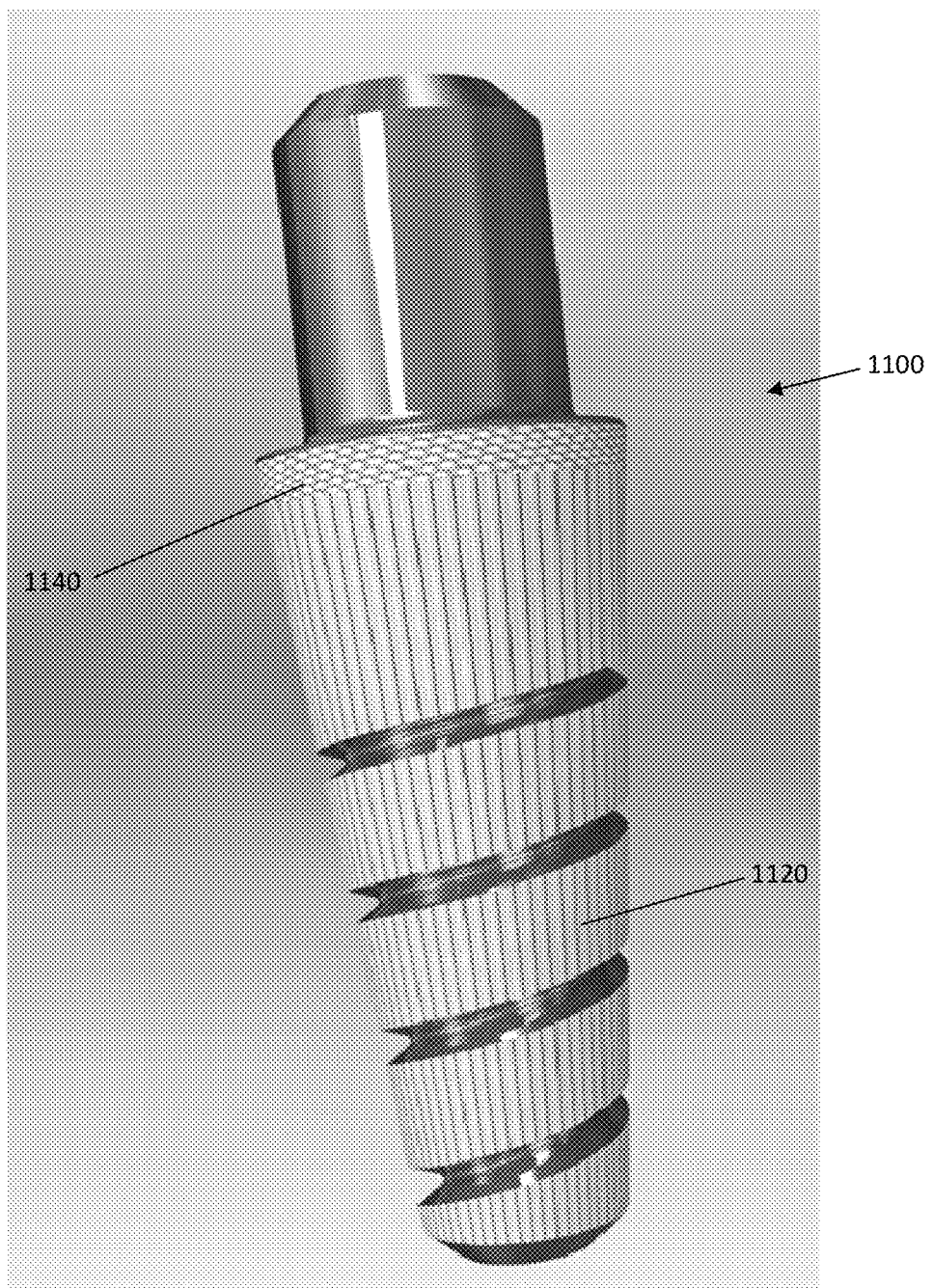
FIG. 11a is an illustration of a dental implant having topographical features imparted by the inventive method.
Figure 11B:
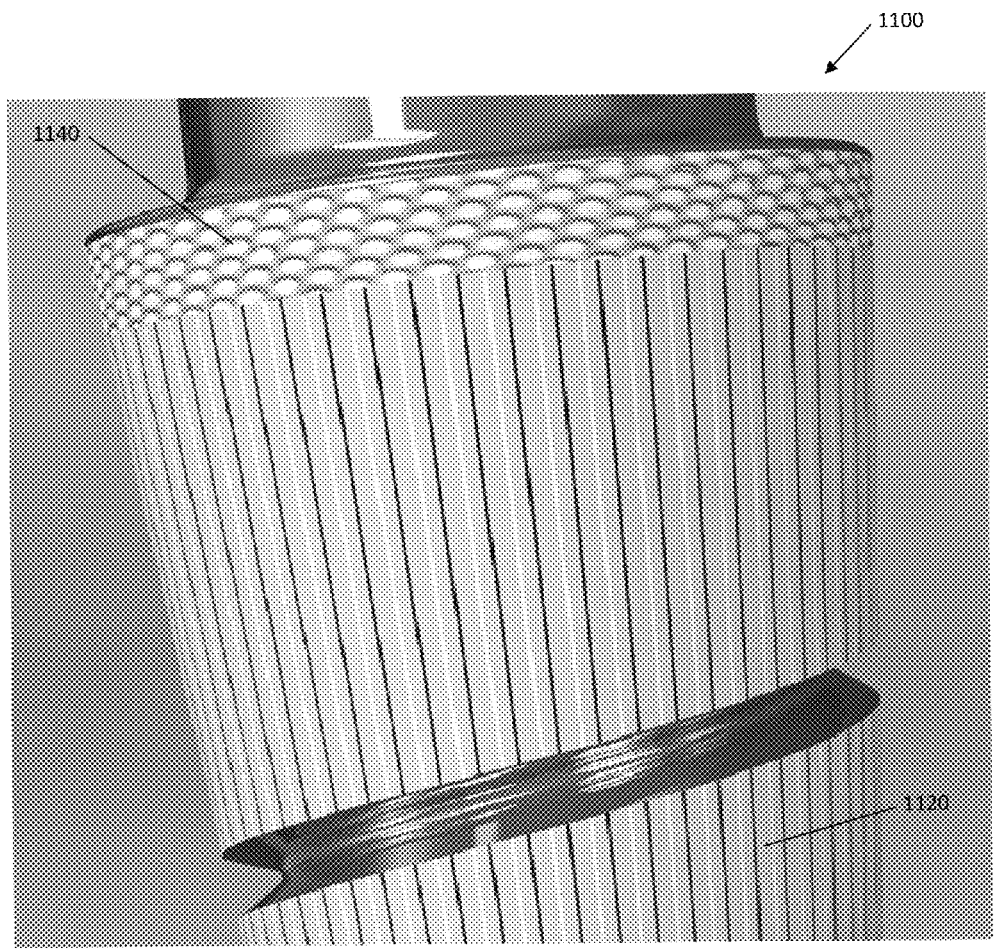

FIG. 11*a* depicts one embodiment of a textured dental implant 1100 having topographical features created thereupon by the inventive method. The dental implant 1100 has a portion imparted with a grooved texture 1120 to promote bone growth in the jaw bone and a portion imparted with a dotted texture 1140 to pin the cells so they don't proliferate into the gums. In the depicted embodiment, the grooves run along the length of the implant 1100, to provide directional migration of cells and thereby promote bone growth along and into the portion of the implant 1100 that is installed into the jaw bone of a patient. The portion of the implant 1100 having a dotted texture 1140 serves to halt the proliferation of cell growth such that the bone growth does not continue into the gums of the patient. The ideal texture for the bone growth may be a crosshatch to add an anchoring effect to the dental implant 1100. FIG. 11*b* is an enlarged view of the grooved portion 1120 and dotted portion 1140 of the dental implant 1100. In alternative embodiments, the features of the grooved portion 1120 may have different arrangements and/or shapes, such as grooves that run diagonally, grooves that run helically, complex geometries that promote bone growth along the length of the implant, features having multiple depths, and/or the like. The portion of the implant 1100 having a dotted texture 1140 may comprise divots, pores, holes, wells, and/or the like, serving to pin cells in place and thereby demote cell proliferation beyond the dotted portion 1140. In alternative embodiments, the features of the dotted portion 1140 may have different arrangements and/or shapes, or the portion may have greater or lesser width or height.

Figure 12A:
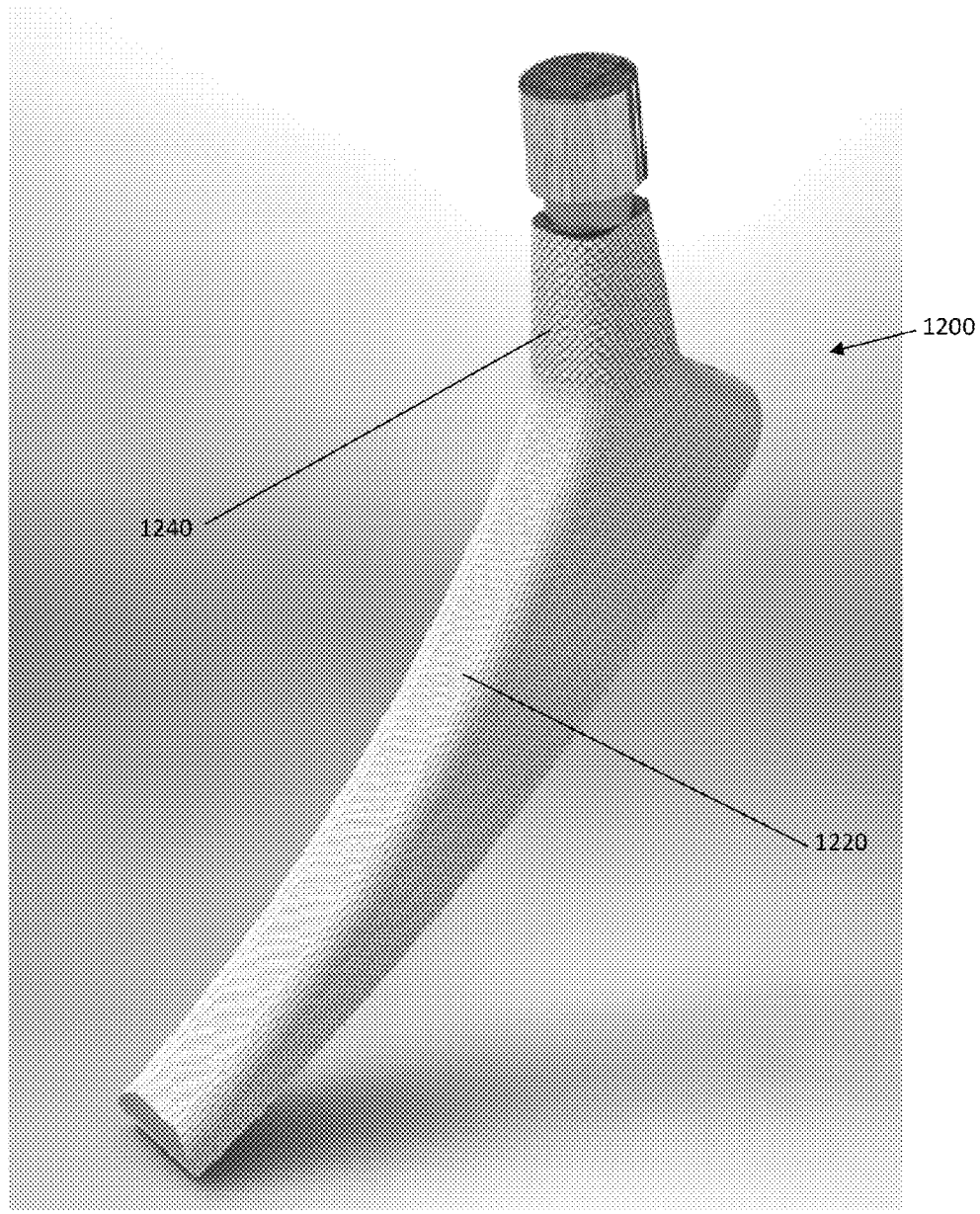
FIG. 12a is an illustration of a hip implant having topographical features imparted by the inventive method.
Figure 12B:
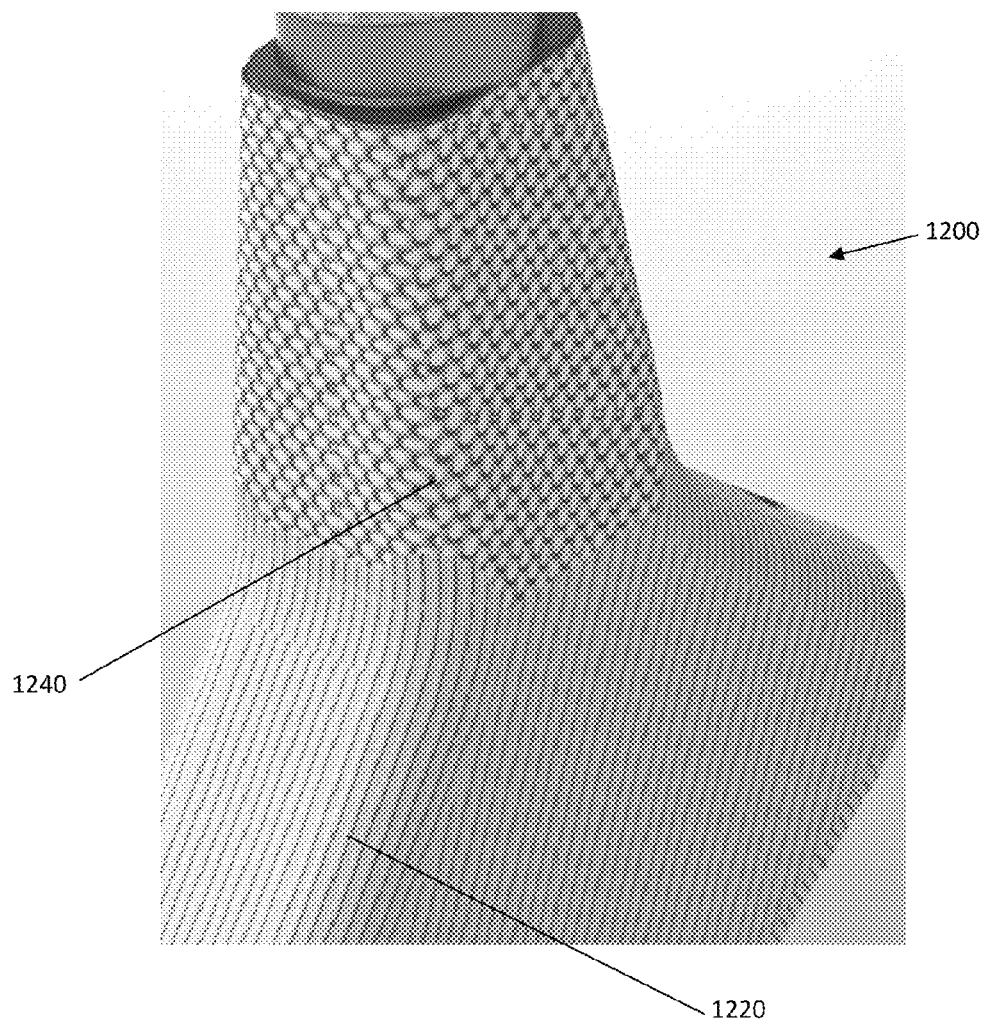
Figure 12C:
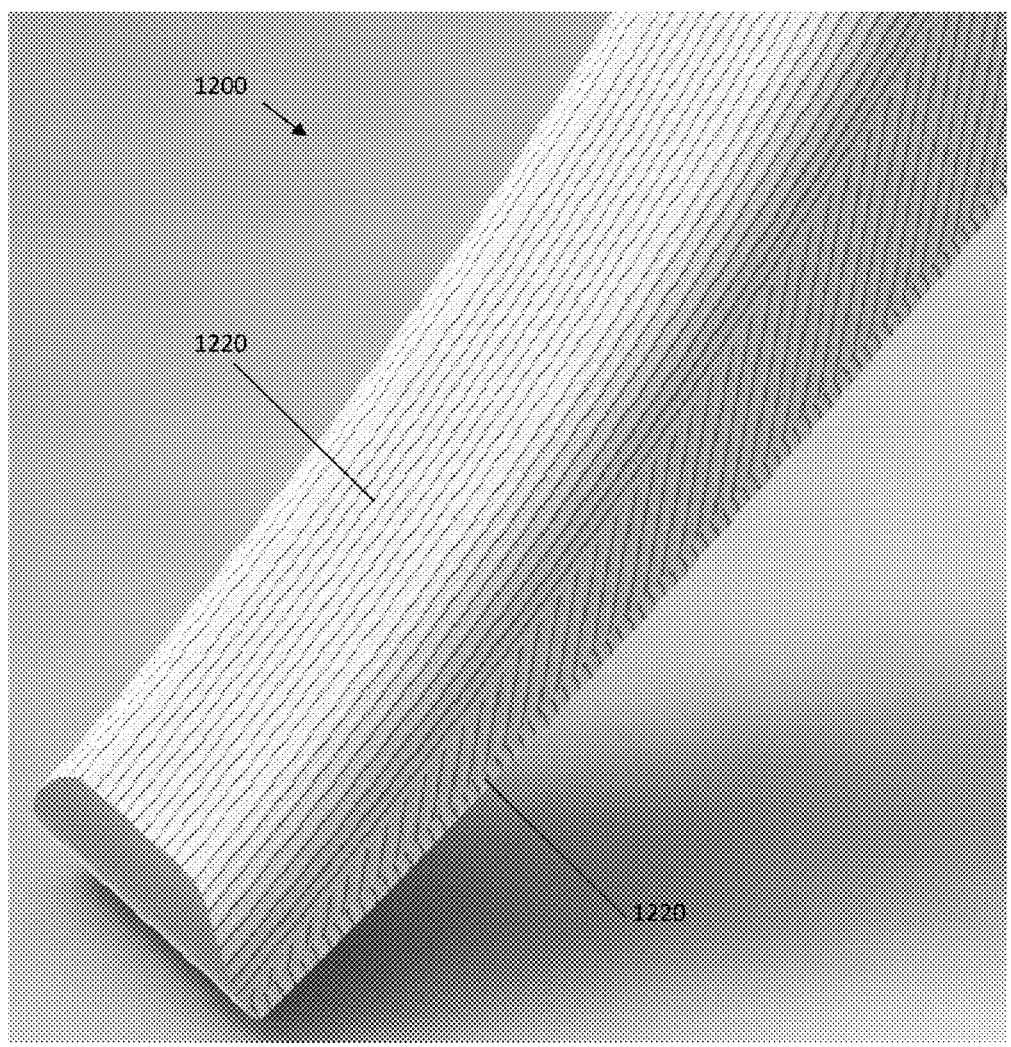

FIG. 12*a* depicts one embodiment of a textured hip implant 1200 having topographical features created thereupon by the inventive method. The hip implant 1200 has a portion imparted with a grooved texture 1220 to promote bone growth and a portion imparted with a dotted texture 1240 to pin the cells so they don't proliferate beyond the dotted portion. In the depicted embodiment, the grooves run along the length of the implant 1200, to provide directional migration of cells and thereby promote bone growth along and into the portion of the implant 1200 that is installed into the bone of a patient. The portion of the implant 1200 having a dotted texture 1240 serves to halt the proliferation of cell growth such that the bone growth does not continue into the joint of the patient. The ideal texture for the bone growth may be a crosshatch to add an anchoring effect to the hip implant 1200. FIG. 12*b* is an enlarged view of the grooved portion 1220 and dotted portion 1240 of the hip implant 1200. In alternative embodiments, the features of the grooved portion 1220 may have different arrangements and/or shapes, such as grooves that run diagonally, grooves that run spirally, complex geometries of features that promote bone growth along the length of the implant, features having multiple depths, and/or the like. The portion of the implant 1200 having a dotted texture 1240 may comprise divots, pores, holes, wells, and/or the like, serving to pin cells in place and thereby demote cell proliferation beyond the dotted portion 1240. In alternative embodiments, the features of the dotted portion 1240 may have different arrangements and/or shapes, or the portion may have greater or lesser width or height. FIG. 12C shows the grooved portion 1220 on the distal portion including a first direction of the grooves and a second direction of the grooves 1220a in direction generally at an angle to the first direction of the grooves.

Figure 13A:
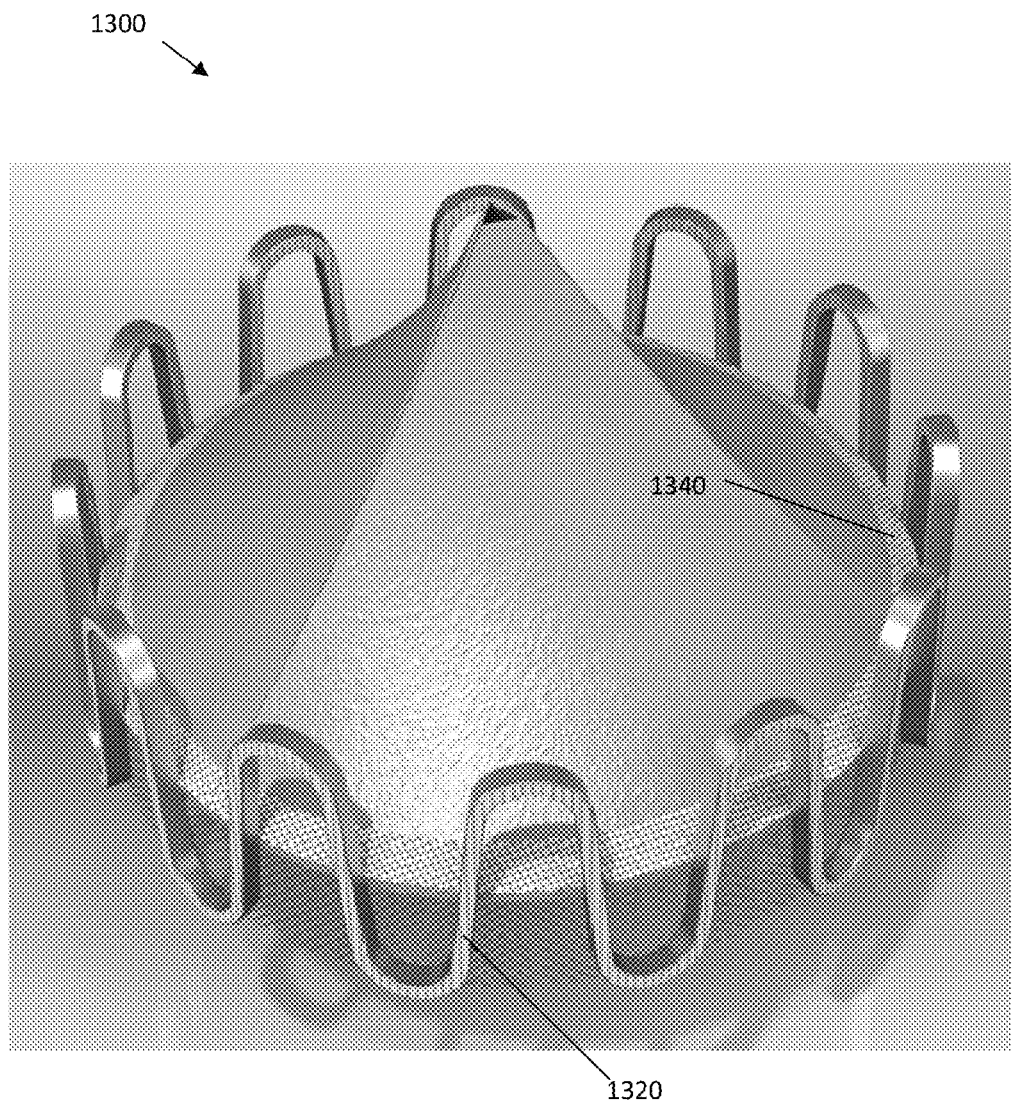
FIG. 13a is an illustration of a heart valve with grooves and dots imparted by the inventive method.
Figure 13B:
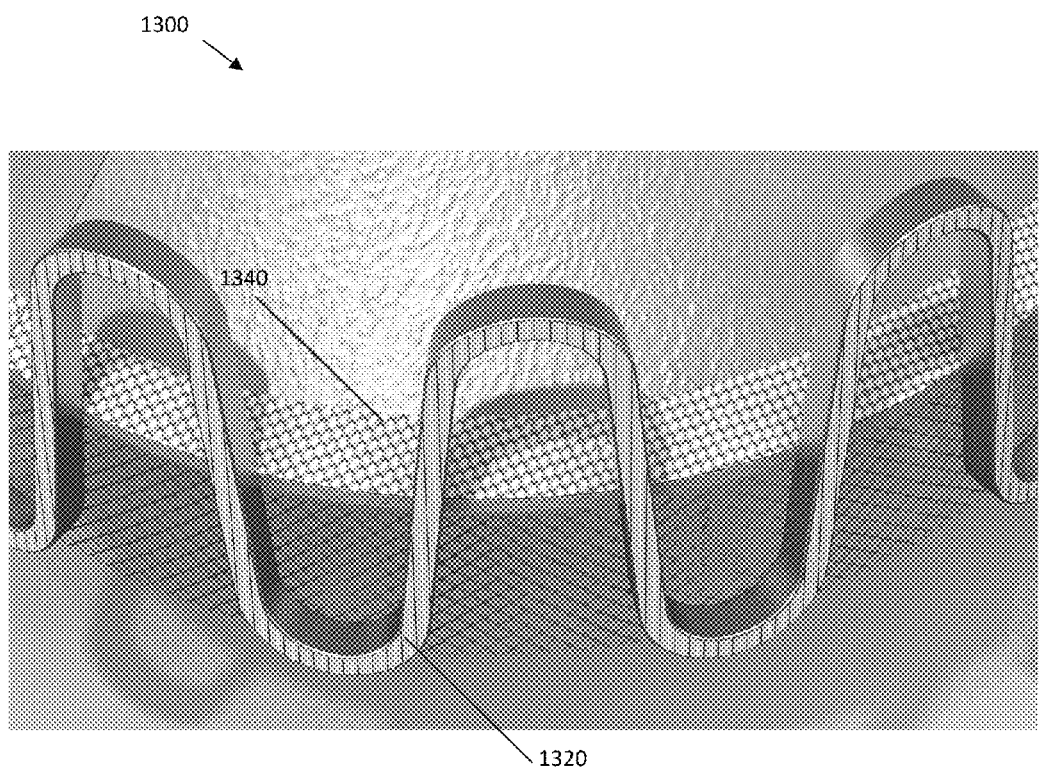

FIG. 13a depicts one embodiment of a textured heart valve 1300 having topographical features created thereupon by the inventive method. The heart valve 1300 has a portion imparted with a grooved texture 1320 to promote cell growth where the heart valve 1300 is anchored to the tissue, and a portion imparted with a dotted texture 1340 to pin the cells so they don't proliferate into the valve portion of the heart valve 1300. In the depicted embodiment, the grooves run along the length of the struts on the heart valve 1300, to provide directional migration of cells and thereby promote cell growth along and into the portion of the implant 1300 that is anchored into the heart of a patient. The portion of the heart valve 1300 having a dotted texture 1340 serves to halt the proliferation of cell growth such that the cell growth does not continue into the valve portion. The ideal texture for the cell growth may be a crosshatch to add an anchoring effect to the heart valve 1300. FIG. 13b is an enlarged view of the grooved portion 1320 and dotted portion 1340 of the heart valve 1300. In alternative embodiments, the features of the grooved portion 1320 may have different arrangements and/or shapes, such as grooves that run diagonally, grooves that run helically, complex geometries that promote cell growth along the length of the implant, features having multiple depths, and/or the like. The portion of the heart valve 1300 having a dotted texture 1340 may comprise divots, pores, holes, wells, and/or the like, serving to pin cells in place and thereby demote cell proliferation beyond the dotted portion 1340. In alternative embodiments, the features of the dotted portion 1340 may have different arrangements and/or shapes, or the portion may have greater or lesser width or height.

It is to be understood that the invention is not limited to the exact details of construction, operation, exact materials, or embodiments shown and described, as obvious modifications and equivalents will be apparent to one skilled in the art. Accordingly, the invention is therefore to be limited only by the scope of the appended claims.

What is claimed:

1. A method of creating structural features on a surface of an article, comprising the steps of:
   a. providing a photomasked transparent apparatus having a mount surface and an open end with at least one fiber optic cable disposed therethrough such that the photomasked transparent apparatus surrounds at least one fiber optic cable;
   b. coating at least the surface of the article with photoresist;
   c. processing the photoresist so as to make it photosensitive;
   d. mounting the photoresist coated article on the mount surface of the photomasked transparent apparatus;
   e. applying the exposing radiation by at least one fiber optic cable through the photomasked transparent apparatus onto the photoresist coated article;
   f. removing the article from the mount surface;
   g. developing the photoresist to reveal the pattern imparted by the photomasked transparent apparatus;
   h. machining the exposed pattern on the article, and
   i. repeating the patterning and machining process with additional photomasked transparent apparatuses to achieve multiple-depth features on the article.

2. The method of claim 1, wherein coating at least the surface of the article with photoresist comprises at least one of dipping, spraying, spinning, and electrodeposition.

3. The method of claim 1, wherein mounting the article on the mount surface further comprises applying an external force to obtain intimate contact between the mount surface and the surface of the article.

4. The method of claim 1, wherein the exposing radiation is a light source.

5. The method of claim 1, wherein machining the exposed pattern comprises at least one of wet chemical etching, dry chemical etching, wet chemical polishing, dry chemical polishing, and electrochemical machining.

6. The method of claim 1, wherein machining the exposed areas comprises machining to a desired depth.

7. The method of claim 1, further comprising, after machining, the step of removing the remaining photoresist from the article, either chemically or mechanically.

8. The method of claim 1, wherein the structural features comprise topographical features.

9. The method of claim 1, wherein the structural features comprise a stent pattern.

10. A method of creating topographical features on the inside surface of a stent, comprising the steps of:
    a. providing a photomasked transparent mandrel having a mount surface and at least one open end with at least one fiber optic cable disposed therethrough such that the photomasked transparent mandrel surrounds at least one fiber optic cable;
    b. coating at least the inside surface of the stent with photoresist;
    c. processing the photoresist so as to make it photosensitive;
    d. mounting the photoresist coated article on the mount surface of the photomasked transparent mandrel;
    e. applying an exposing radiation by at least one fiber optic cable through the photomasked transparent mandrel onto the photoresist coated stent;
    f. removing the stent from the photomasked mandrel;
    g. developing the photoresist to reveal the pattern imparted by the photomasked mandrel;
    h. machining the exposed pattern on the stent; and
    i. repeating the patterning and machining process with additional photomasked mandrels to achieve multiple-depth features on the stent.

11. The method of claim 10, wherein coating at least the inside surface of the stent with photoresist comprises at least one of dipping, spraying, spinning, and electrodeposition.

12. The method of claim 10, wherein mounting the stent on the mandrel further comprises applying an external force to obtain intimate contact between the mandrel and the inner surface of the stent.

13. The method of claim 10, wherein mounting the stent on the mandrel further comprises utilizing an interference fit between the mandrel and the stent to obtain intimate contact between the mandrel and the inner surface of the stent.

14. The method of claim 13, wherein the interference fit is obtained by shape memory when the stent is nitinol-based.

15. The method of claim 10, wherein the exposing radiation is a light source.

16. The method of claim 10, wherein machining the exposed pattern comprises at least one of wet chemical etching, dry chemical etching, wet chemical polishing, dry chemical polishing, and electrochemical machining.

17. The method of claim 10, wherein machining the exposed areas comprises machining to a desired depth.

* * * * *